(12) United States Patent
Matthae et al.

(10) Patent No.: US 8,378,314 B2
(45) Date of Patent: Feb. 19, 2013

(54) DEVICE AND METHOD FOR THE EVANESCENT ILLUMINATION OF A SAMPLE

(75) Inventors: Manfred Matthae, Jena (DE); Bruene Venus, Goettingen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 284 days.

(21) Appl. No.: 12/991,108

(22) PCT Filed: Apr. 28, 2009

(86) PCT No.: PCT/EP2009/003056
§ 371 (c)(1),
(2), (4) Date: Nov. 4, 2010

(87) PCT Pub. No.: WO2009/135607
PCT Pub. Date: Nov. 12, 2009

(65) Prior Publication Data
US 2011/0062348 A1 Mar. 17, 2011

(30) Foreign Application Priority Data
May 7, 2008 (DE) .......................... 10 2008 022 493

(51) Int. Cl.
*G01N 21/64* (2006.01)
(52) U.S. Cl. .................................... 250/458.1
(58) Field of Classification Search ............... 250/458.1, 250/492.1, 372; 356/320; 359/362
See application file for complete search history.

(56) References Cited

U.S. PATENT DOCUMENTS

| 5,184,251 | A | 2/1993 | Tsuchida et al. |
| 6,051,437 | A | 4/2000 | Luo et al. |
| 6,124,981 | A | 9/2000 | Ogawa |
| 6,287,871 | B1 | 9/2001 | Herron et al. |
| 7,227,704 | B2 | 6/2007 | Koike |
| 7,260,251 | B2 | 8/2007 | Dowski, Jr. et al. |
| 7,835,076 | B2 | 11/2010 | Roorda et al. |
| 2003/0086067 | A1 | 5/2003 | Gerstner et al. |
| 2004/0174523 | A1 | 9/2004 | Uhl et al. |
| 2005/0179903 | A1 | 8/2005 | Tsuruta et al. |
| 2006/0203354 | A1 | 9/2006 | Fujimoto et al. |
| 2009/0034061 | A1 | 2/2009 | Dodoc et al. |

FOREIGN PATENT DOCUMENTS

| DE | 1 096 634 A | 1/1961 |
| DE | 60 2005 003 665 T2 | 11/2008 |
| DE | 10 2007 047 466 A1 | 4/2009 |
| EP | 1 801 798 A1 | 6/2007 |
| KR | 10 2006 0104566 A | 10/2006 |
| WO | WO 97/35181 | 9/1997 |
| WO | WO 2004/090581 A2 | 10/2004 |
| WO | WO 2007/050743 A2 | 5/2007 |
| WO | WO 2008/009581 A1 | 1/2008 |
| WO | WO 2009/043546 A1 | 4/2009 |

*Primary Examiner* — David Porta
*Assistant Examiner* — Faye Boosalis
(74) *Attorney, Agent, or Firm* — Patterson Thuente Christensen Pedersen, P.A.

(57) ABSTRACT

A device for the evanescent illumination of a sample, including an optical illumination element with an optical corrective element and an objective arranged downstream from the corrective element, to evanescently illuminate the sample with a supplied ray beam containing optical radiation with at least two different wavelengths. The corrective optical element has a transverse chromatic aberration which, during the illumination, leads to the optical radiation penetrating the pupil of the objective at different heights relative to the optical axis varying according to the wavelength. The corrective optical element is selected in such a way that the wavelength-related difference of the penetration depths of the radiation into the sample is reduced during the evanescent illumination.

15 Claims, 5 Drawing Sheets

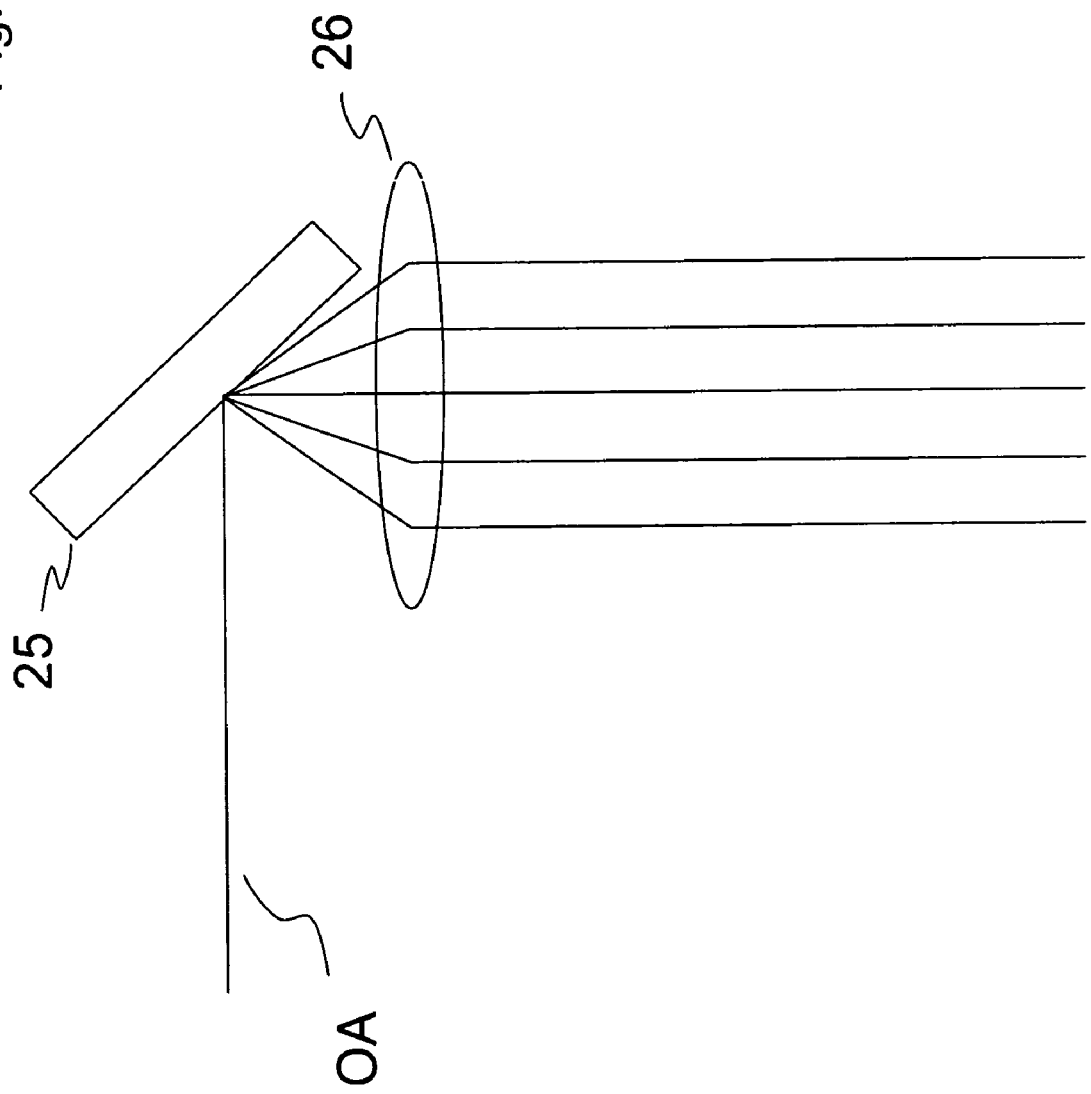

DEVICE AND METHOD FOR THE EVANESCENT ILLUMINATION OF A SAMPLE

PRIORITY CLAIM

The present application is a National Phase entry of PCT Application No. PCT/EP2009/003056, filed Apr. 28, 2009, which claims priority from German Application Number 102008022493.6, filed May 7, 2008, the disclosures of which are hereby incorporated by reference herein in their entirety.

FIELD OF THE INVENTION

The invention relates to a device and a method for the evanescent illumination of a sample.

BACKGROUND

In the evanescent illumination of a sample, the ray bundle for illuminating the sample is supplied in such a way that total reflection occurs on the boundary surface to the sample. A standing evanescent wave is thus formed in the sample, the intensity of which decreases exponentially with the distance to the boundary surface.

The distance at which the intensity has dropped to the $1/e^{th}$ part can be defined as the distance which describes the penetration depth of the evanescent wave. Typical values lie in the range of 100 to 200 nm.

The evanescent radiation is used for exciting fluorescence in the sample for example. The excited fluorescence radiation can then be detected by means of a microscope.

Increasingly, several fluorescences with different wavelengths are to be excited. This should occur under the same conditions to the highest possible extent, so that the individual fluorescence images remain meaningful and can be combined with one another or compared with one another quantitatively. The difficulty occurs in this connection that the penetration depth of the evanescent illumination depends on the wavelength and the incidence angle. The penetration depths are different for different wavelengths at the same incidence angle.

SUMMARY OF THE INVENTION

On the basis of this, it is the object of the present invention to provide a device for the evanescent illumination of a sample in which the wavelength-related differences of the penetration depths are reduced. Furthermore, a respective method for the evanescent illumination of a sample is provided.

The object is achieved by a device for the evanescent illumination of a sample, with the device comprising an illumination optics provided with a correction optics and an objective arranged downstream from said correction optics and evanescently illuminating the sample with a supplied ray bundle containing optical radiation with at least two different wavelengths, with the correction optics having a transverse chromatic aberration which, during illumination, leads to the optical radiation traversing the pupil of the objective at different heights according to the wavelength, and which is selected in such a way that the wavelength-related difference of the penetration depths of the radiation into the sample is reduced during the evanescent illumination.

As a result, the device in accordance with the invention can be used to illuminate the sample simultaneously with the optical radiation with at least two different wavelengths or with pencil of rays with two different wavelengths, which is advantageous in the case of fluorescence examinations for example. The differences in the penetration depths can be reduced considerably, through which multi-spectral images from frequency excitations performed simultaneously or sequentially can be evaluated for example.

The spectral penetration depths in evanescent illumination are thus unified with the device in accordance with the invention. It is thus advantageously no longer necessary to provide an adjustment option for aligning the spectral penetration depths in the apparatus.

It is exploited advantageously in the device in accordance with the invention that the height of the objective pupil influences the illumination angle and thus the penetration depth in evanescent illumination. This is utilized in accordance with the invention by the intentional chromatic difference in magnification of the correction optics in the manner that the necessary wavelength-dependent heights in the objective pupil are present in order to achieve the same penetration depths during evanescent illumination.

As a result of the device in accordance with the invention, the measurements or examinations can be performed with a considerably higher frequency in the case of experiments, for example in which different fluorophores or dyestuffs are to be excited simultaneously or sequentially with different wavelengths, because no mechanical elements need to be moved any more between two examinations (or snapshots) as was necessary before in order to reach the same penetration depths or the same excitation volume.

The correction optics can comprise diffractive and/or refractive elements. In particular, correction optics can be an obliquely positioned planar plate, a wedge, a prism, a diffracting element and/or a lens which can be obliquely positioned, and any combination of these elements. The transverse chromatic aberration caused by the correction optics can especially also be chosen by consideration of the magnification of the objective. Should the objective have a chromatic aberration in the illumination, this can be considered in the choice of the transverse chromatic aberration or the chromatic difference in magnification of the correction optics.

The correction optics can have a plane conjugated to the objective pupil, with the supplied ray bundle running through the same. In particular, the supplied ray bundle runs parallel to the optical axis of the correction optics through the conjugated plane. The arrangement of the correction optics is easily possible in this case.

Furthermore, the ray bundle can pass through this plane in an off-axis manner at a distance and under an angle as corresponds to the required travel path of the chief ray in the objective pupil. Light of different wavelengths can be supplied in this plane within an optical fiber for example, which light is imaged in accordance with the invention in the objective pupil with the defined transverse chromatic aberration, through which the spectral differences in the penetration depths can be reduced in a purposeful manner.

In particular, the device in accordance with the invention for the evanescent illumination of a sample can comprise a feed unit which feeds the ray bundle of the correction optics in an off-axis manner and/or in such a way that it does not extend parallel to the optical axis of the correction optics. The feed unit may comprise an optical fiber, the fiber end of which is positioned in such a way that the desired feed of the ray bundle is realized. It is understood that the feed unit can also contain other optical elements such as beam splitters, lenses, gratings, etc.

In the supplied ray bundle, the ray pencils with the different wavelengths can be contained coaxially with respect to one another. This simplifies the configuration of the correction optics.

The device in accordance with the invention for the evanescent illumination of a sample can further have an actuating element which can be a part of the feed unit, for example and with which the position and/or the angle of the ray bundle can be set in which or under which it passes through the conjugated plane. In particular, the distance of the ray bundle to the optical axis of the correction optics can be changed. It is thus possible to change the penetration depth for all wavelengths simultaneously.

The actuating element can also be arranged in such a way that all wavelength-dependent heights in the objective pupil can thus be changed simultaneously. The change can be effected in such a way that the penetration depth is changed in a wavelength-independent manner. A slight wavelength-dependent change of the spectral penetration depths can occur in case of a change of the penetration depth by the actuating element. The remaining difference is lower by at least one magnitude in comparison with the non-corrected case.

When the supplied ray bundle contains two or more ray pencils with different wavelengths, the wavelength-related differences in the penetration depths can be minimized. It is especially possible that the penetration depths for two, three or more wavelengths are the same. In the case of wavelengths that lie in between, a considerable reduction is possible in comparison with the case in which no correction of the penetration depths is performed whatsoever. The remaining difference can be lower by one or several magnitudes than in comparison with the non-corrected case.

In the case of more than two or three different wavelengths, the corrective optical element can be arranged in such a way, for example, that the spectral differences are minimized for all wavelengths. It can be demanded for example that the spectral difference does not exceed a predetermined limit value for any of the wavelengths. Any other kind of minimization is also possible.

Optical radiation or optical ray pencils shall especially be understood herein to be electromagnetic radiation which behaves according to optical laws. In particular, it concerns radiation from the visible wavelength range. Radiation from the infrared range or the UV range is also possible.

The device in accordance with the invention for the evanescent illumination of a sample can be the component of a microscope. In this case, a microscope is provided which can evanescently illuminate the sample in such a way that wavelength-related differences in the penetration depth of the radiation in the sample are reduced.

In this case, the correction optics can utilize a part of the illumination optics of the microscope. The correction optics can contain a part of the incident vertical illumination arranged downstream of the objective. In this case, the correction optics contains a correction module for example which can be added to the microscope and which realizes the correction optics in accordance with the invention together with the part of the illumination optics. In this case, the correction optics is preferably arranged in such a way that the desired transverse chromatic aberration of the correction optics is realized together with the part of the utilized illumination optics.

When fluorescence radiation is detected with such a microscope, it is often also called a TIRF microscope (=Total Internal Reflection Fluorescence). In a TIRF microscope, the background fluorescence known from epi-fluorescence is reduced considerably and the image contrast is improved considerably. The result is a respectively high z-resolution. The evanescent field has a typical thickness of 100 to 200 nm.

The device in accordance with the invention allows optimizing the spectral excitation volumes in a TIRF microscope and process with several different wavelengths in order to obtain more brilliant and better TIRF color images by utilizing the several wavelengths.

As a result of the imaging principle, this illumination method of the device in accordance with the invention is especially suitable for examining dynamic processes in the environment of the cell membrane and for examining the interactions of molecule to molecule in the cell-free system. Furthermore, the combination of electrophysiological and pharmacological experiments (manipulation of the sample) will also play a major role because TIRF microscopy is capable of supplying images where previously only indirect measurements were possible.

The device in accordance with the invention for the evanescent illumination of a sample can further comprise a source for the generation of the ray bundle. The radiation can especially concern laser radiation.

The device in accordance with the invention for the evanescent illumination of a sample and the microscope with such a device can contain a control device known to the person skilled in the art. The microscope can especially be arranged in the conventional manner.

The object is further achieved by a method for the evanescent illumination of a sample, comprising a ray bundle containing optical radiation with at least two different wavelengths, with the ray bundle being directed to a sample via a correction optics and an objective arranged downstream of the correction optics in such a way that it is illuminated evanescently, with the correction optics having a transverse chromatic aberration which, during illumination, leads to the optical radiation traversing the pupil of the objective at different heights according to the wavelengths, and which is selected in such a way that the wavelength-related difference of the penetration depths of the radiation into the sample is reduced during the evanescent illumination.

The method in accordance with the invention allows illuminating the sample evanescently with different wavelengths simultaneously and ensuring that the penetration depths differ only slightly. In one embodiment of the invention the penetration depths can be the same.

The same illumination conditions with different wavelengths can be achieved in an outstanding fashion with such a method.

The correction optics can be provided with at least one refractive and/or at least one diffractive element.

In particular, the correction optics can comprise a plane conjugated to the pupil of the objective, with the supplied ray bundle passing through the same. Preferably, the ray bundle passes through the conjugated plane as a coaxial ray beam for the different wavelengths.

In the method, the sample is preferably illuminated with the optical radiation with the different wavelengths simultaneously.

The method can be used for supplying the ray bundle to the correction optics in an off-axis manner and/or in such a way that it does not extend parallel to the optical axis of the correction optics. The transverse chromatic aberration of the correction optics can thus be utilized in a purposeful manner in such a way that the different wavelengths pass through the pupil of the objective at the desired different heights.

The illumination method in accordance with the invention can be used in microscopic examinations. A respective microscopy method, e.g. a TIRF microscopy method, is thus provided. The microscopy method can be further developed in the manner known to the person skilled in the art.

It is understood that the features as mentioned above and yet to be explained below can be used not only in the stated combinations but also in other combinations or alone without leaving the scope of the present invention.

BRIEF DESCRIPTION OF THE DRAWINGS

The invention will be explained below in closer detail by reference to the enclosed drawings which also disclose features relevant to the invention, wherein:

FIG. 6 is a further embodiment of the device in accordance with the invention for the evanescent illumination of a sample by using a grating acting in a diffractive manner.

DETAILED DESCRIPTION

Figure 1:
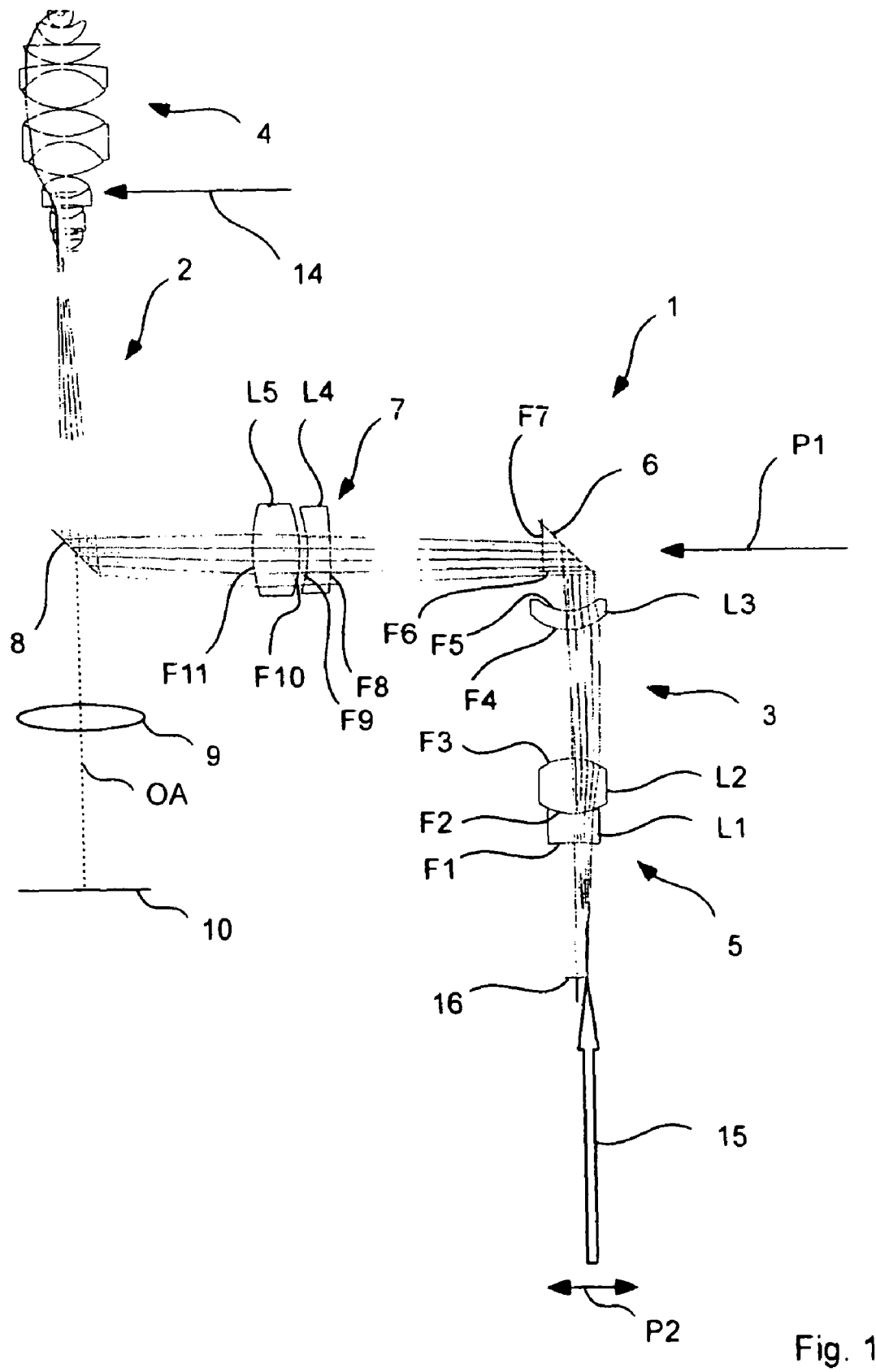
FIG. 1 is a schematic view of an embodiment of the device in accordance with the invention for the evanescent illumination of a sample.
Figure 2:
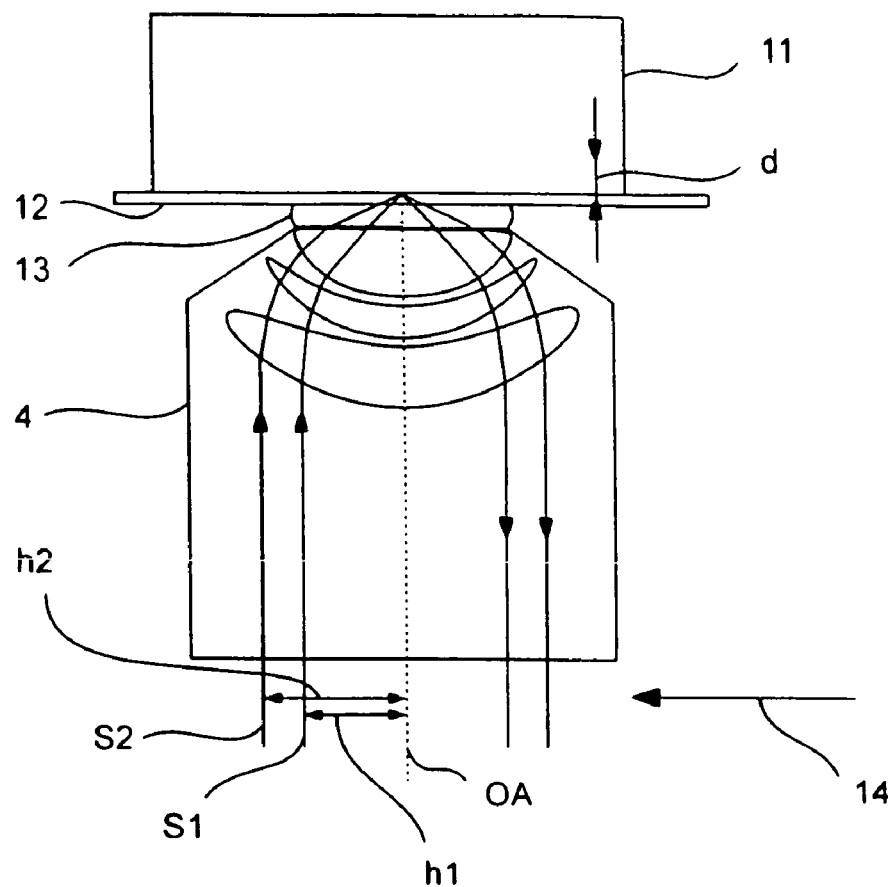
FIG. 2 is an enlarged view of the objective 4 with sample 11 of FIG. 1.

In the embodiment depicted in FIGS. 1 and 2, the device 1 in accordance with the invention for the evanescent illumination of a sample is integrated in a microscope 2 and comprises a correction optics 3 and an objective 4 arranged downstream of the correction optics 3.

The correction optics 3 comprises a correction unit 5 with three lenses L1, L2 and L3, a downstream deflecting prism 6, an incident light optics 7 with two lenses L4 and L5, and a reflecting mirror 8.

The incident light optics 7 can be the component of a conventional incident vertical illumination for the microscope 2. Further elements of incident vertical illumination are not shown here for reasons of simplicity of the illustration. The light for the incident vertical illumination would meet the incident light optics 7 from the direction indicated by arrow P1 if prism 6 were removed, and then be fed into the microscope beam path via the reflecting mirror 8. The reflecting mirror 8 can be arranged as a partly transparent reflecting mirror and/or dichroic reflecting mirror (depending on the application).

The microscope 2 can further comprise a tube optics 9 and an image sensor 10.

In the embodiment according to FIGS. 1 and 2, an evanescent illumination of the sample 11 is performed with radiation 15 with the wavelengths 450 and 575 nm in such a way that the penetration depth is 93 nm in each case, irrespective of the two wavelengths. The supplied ray bundle 15 is illustrated in FIG. 1 by an arrow. The tip of the arrow lies in a plane 16 and can be the fiber end for example from which the radiation 15 exits.

The correction optics 3 is arranged in this case in such a way that the plane 16 is a conjugated plane to the exit pupil 14 of objective 4, the position of which is indicated in FIG. 1 by arrow 14. Furthermore, the correction optics 3 comprises a transverse chromatic aberration which is configured in such a way that in this way the wavelength-dependent differences of the penetration depth d (FIG. 2) in the evanescent illumination of the sample 11 to be examined is compensated for the two wavelengths 450 nm and 575 nm.

In order to achieve the same predetermined penetration depth d of 93 nm for the two wavelengths 450 nm and 575 nm, the correction unit 5 of the correction optics 3 is arranged in such a way that it has a strong transverse chromatic aberration. The transverse chromatic aberration is chosen in such a way that the optical radiation or the optical ray pencil S1 with the wavelength 450 nm passes through the pupil 14 of objective 4 on the detection side at a lower height h1 (distance to optical axis OA) than the optical radiation S2 with the wavelength of 575 nm, as is indicated schematically in FIG. 2. The different heights h1, h2 (distances to the optical axis OA) are predetermined by the correction unit 5 in such a way that as a result of the thus resulting different angles of incidence of the radiation S1, S2 on the sample 11 the penetration depth d is 93 nm each for both wavelengths.

The correction unit 5 is arranged depending on the heights h, which can be calculated as follows based on the desired penetration depth d:

The penetration depth d can be represented according to the following formula 1:

$$d = \frac{\lambda}{4\pi n_2 \sqrt{(\sin\alpha/\sin\alpha_g)^2 - 1}} \quad (1)$$

$\lambda$ stands for the wavelength of the used optical radiation, $\alpha$ for the current angle of beam incidence, $\alpha_g$ for the critical angle of beam incidence for the transition to total reflection, and $n_2$ for the refractive index of the sample (i.e. the medium which is illuminated evanescently).

The critical angle $\alpha_g$ of total reflection can be represented according to the following formula 2:

$$\sin\alpha_g = \frac{n_2}{n_1} \quad (2)$$

wherein $n_1$ is the refractive index of the cover glass 12.

When formulas 1 and 2 are linked together, the penetration depth of the evanescent wave into sample 11 can be represented as follows:

$$d = \frac{\lambda}{4\pi \sqrt{n_1^2 \sin^2\alpha - n_2^2}}. \quad (3)$$

If the penetration depth d is to be the same for different wavelengths, it can be demanded from formula 3 that the following expression must be constant.

$$\frac{n_1^2 \sin^2\alpha - n_2^2}{\lambda^2}. \quad (4)$$

The value $n_1 \cdot \sin\alpha$ corresponds to the aperture on the object side in objective 4. This leads to the following formula under inclusion of the sine condition at infinite image distance:

$$h = (n_1 \sin\alpha)f \quad (5)$$

wherein h is the height of the respective aperture beam in the exit pupil 14 of objective 4 and f is the focal length of the objective 4.

The required apertures ($n_1 \cdot \sin \alpha$) on the object side for a determined or desired penetration depth can be calculated for the individual wavelengths from the formula 3. Formula 5 produces the wavelength-dependent heights h for the light incidence into the exit pupil 14 of objective 4. When the wavelength-dependent heights h are known, the chromatic magnification aberration resulting from the correction unit 5 can be designed in such a way that the optical rays S1, S2 with the different wavelengths of the ray bundle 15 supplied to the correction unit 5 pass through the exit pupil 14 at the calculated heights h.

Furthermore, the axial distance of the ray bundle 15 from the optical axis of the correction optics 3 can be changed in the device of FIG. 1, as is indicated by the double arrow P2. The penetration depth can be varied via this change of distance. The change of distance can occur especially via an actuator (not shown).

When the penetration depth is set in this manner to a value other than the 93 nm as assumed here, a reduction of the different wavelength-dependent penetration depths is still achieved by means of the correction unit 5. It may occur however that the penetration depths are no longer precisely the same. However, the difference of the penetration depths is considerably lower in comparison with a case without the corrective unit 5 in accordance with the invention.

The following Table 1 shows the radii and distances of the individual areas of the lenses L1 to L5 and the respective refractive index of the used lens materials.

TABLE 1

| Surface | Radii (mm) | Thicknesses/distances to next surface (mm) | Refractive index (for 514.5 nm) |
|---|---|---|---|
| 16 | ∞ | 27.464 | 1 |
| F1 | −33.4951 | 5.96 | 1.73004 |
| F2 | 12.32 | 11.28 | 1.435962 |
| F3 | −12.32 | 27.109 | 1 |
| F4 | 10.903 | 4.07 | 1.612309 |
| F5 | 9.173 | 8.46 | 1 |
| F6 | ∞ | 10 | 1.52049 |
| F7 | ∞ | 44.02 | 1 |
| F8 | 86.5932 | 4.6 | 1.644665 |
| F9 | 24.938 | 1.725 | 1 |
| F10 | 28.184 | 9.63 | 1.501224 |
| F11 | −32.543 | 111.139 | 1 |
| 14 | | | |

Figure 3:
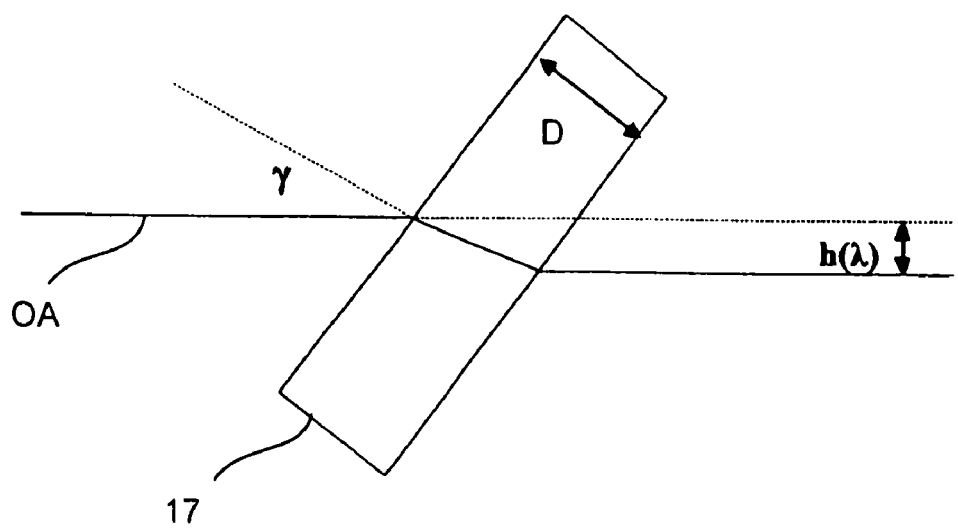
FIG. 3 is a further embodiment of the device in accordance with the invention for the evanescent illumination of a sample.

Another possible correction unit 5 is shown in FIG. 3. In this case, the correction unit comprises an inclined planar plate 17 and compensates the chromatic differences of the penetration d for 425 nm and 575 nm.

Figure 5:
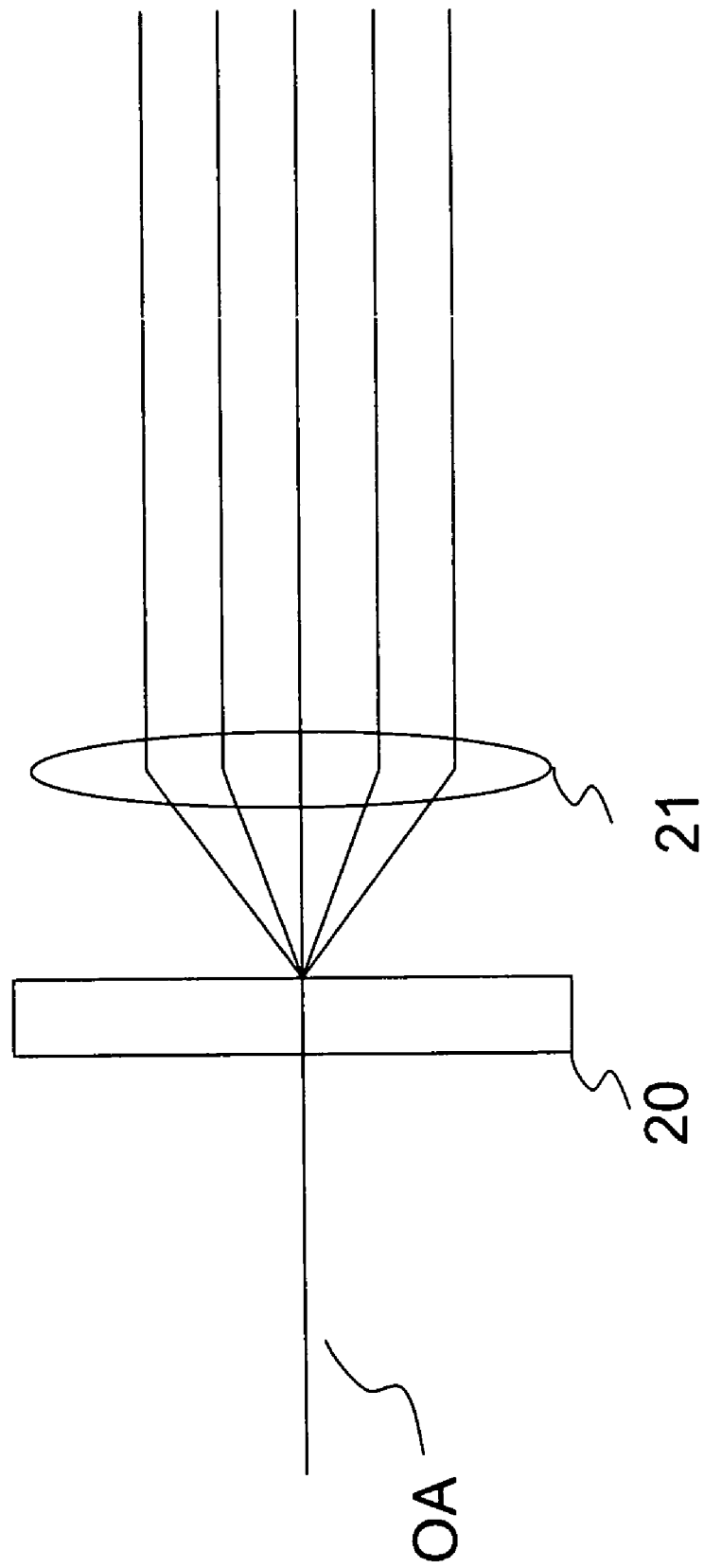
FIG. 5 is a further embodiment of the device in accordance with the invention for the evanescent illumination of a sample by using a diffractive optics.

Further possible correction units are shown in FIGS. 5 and 6. In FIG. 5, the ray bundle fed to the correction optics passes through a diffractive optics (20) which leads to a wavelength-dependent splitting of the radiation. The light is collimated by a downstream lens 21 whose focal point lies in the point of impact of the supplied ray bundle on the diffractive optics.

In FIG. 6, the ray bundle fed to the correction optics meets a diffractively acting grating 25, leading to a wavelength-dependent splitting of the radiation. The light is collimated by a downstream lens 26 whose focal point lies in the point of incidence of the supplied ray bundle on the diffractive grating.

The height difference $\Delta h(\lambda)$ to be achieved for the wavelengths 425 nm and 575 nm is 0.0989 mm at a penetration depth of 93 nm when using objective 4. Such a height difference is achieved when the ray bundle 15 with the optical radiation meets the planar plate 17 under an angle $\gamma$ of 37.149° with these two wavelengths. Since the optical radiation is refracted differently depending on its wavelength, the optical rays with the different wavelengths leave the planar plate 17 in a parallel offset manner with different heights $h(\lambda)$. The height difference required here is reached with a thickness D of the planar plate 17 of 17.775 mm.

Figure 4:
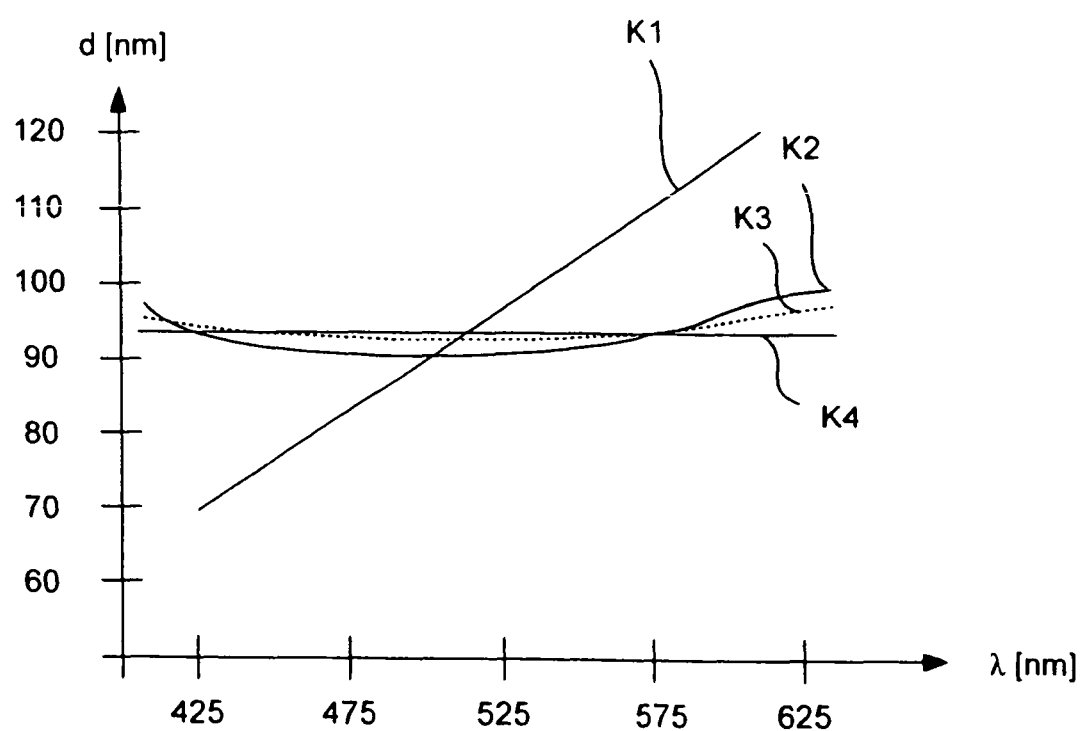
FIG. 4 is a diagram for the explanation of the present penetration depths in the embodiments of FIGS. 1 to 3.

FIG. 4 shows the penetration depths in evanescent illumination for different cases. Curve K1 shows the penetration depth depending on the wavelength without correction in accordance with the invention. Curve K2 shows the penetration depths for the embodiment of FIG. 1. Curve K3 with the broken line shows the penetration depths for a correction optics (not shown), in which an optimization of the pupil heights was performed with eight wavelengths between 400 and 650 nm. Such a correction optics comprises an additional lens in comparison with the correction optics 3 of FIG. 1. Finally, the wavelength-independent penetration depth of 93 nm is shown as curve K4.

The achieved adjustment of the penetration depths can be seen clearly from the illustration of the penetration depths.

The invention claimed is:

1. A device for the evanescent illumination of a sample, comprising:
   illumination optics including correction optics and an objective arranged downstream from said correction optics that evanescently illuminate the sample with a supplied ray bundle having optical radiation of at least two different wavelengths;
   the correction optics having a transverse chromatic aberration which, during illumination, leads to the optical radiation traversing the pupil of the objective at different heights measured from an optical axis of the objective, the heights being different relative to the wavelength, and
   the transverse chromatic aberration of the correction optics being selected such that the wavelength-related difference of penetration depths of the radiation into the sample is reduced during the evanescent illumination.

2. The device according to claim 1, wherein the correction optics comprises at least one refractive element.

3. The device according to claim 1, wherein the correction optics comprises at least one of an obliquely positioned planar plate and an obliquely positioned lens.

4. The device according to claim 1, wherein the correction optics comprises a plane conjugated to the objective pupil, with the supplied ray bundle passing through said plane.

5. The device according to claim 1, comprising a feed unit which feeds the ray bundle to the correction optics in an off-axis manner.

6. The device according to claim 5, wherein the feed unit feeds the ray bundle of the correction optics in such a way that it does not extend parallel to the optical axis of the correction optics.

7. The device according to claim 1, wherein the correction optics comprises at least one diffractive element.

8. A method of evanescent illumination of a sample, comprising:
   directing a ray bundle containing optical radiation of at least two different wavelengths to a sample via correction optics and an objective arranged downstream from the correction optics such that the sample is illuminated evanescently;
   selecting the correction optics to have a transverse chromatic aberration which, during illumination, leads to the optical radiation traversing the pupil of the objective at different heights varying according to the wavelength, the different heights being measured relative to an optical axis of the objective; and selecting the transverse chromatic aberration such that the wavelength-related difference of penetration depths of the radiation into the sample is reduced during the evanescent illumination.

9. The method according to claim 8, further comprising providing the correction optics with at least one refractive element and with at least one of an obliquely positioned planar plate and an obliquely positioned lens.

10. The method according to claim 8, further comprising arranging the correction optics to have a plane conjugated to the objective pupil, with the supplied ray bundle passing through said plane.

11. The method according to claim 10, further comprising arranging the delivery of the ray bundle that contains the optical radiation such that the ray bundle passes the conjugated plane as a coaxial ray bundle.

12. The method according to claim 8, further comprising illuminating the sample with at least two wavelengths of the optical radiation simultaneously.

13. The method according to claim 8, further comprising feeding the ray bundle to the correction optics in an off-axis manner.

14. The method according to claim 8, further comprising feeding the ray bundle to the correction optics such that ray bundle does not extend parallel to the optical axis of the correction optics.

15. The method according to claim 8, further comprising providing the correction optics with at least one diffractive element.

* * * * *

UNITED STATES PATENT AND TRADEMARK OFFICE
CERTIFICATE OF CORRECTION

PATENT NO. : 8,378,314 B2  
APPLICATION NO. : 12/991108  
DATED : February 19, 2013  
INVENTOR(S) : Manfred Matthae et al.

It is certified that error appears in the above-identified patent and that said Letters Patent is hereby corrected as shown below:

In the Specification

Col. 6, line 31, delete "a" and insert --α--

Signed and Sealed this  
Thirty-first Day of December, 2013

Margaret A. Focarino  
*Commissioner for Patents of the United States Patent and Trademark Office*